(12) United States Patent
Dykstra et al.

(10) Patent No.: US 6,815,461 B1
(45) Date of Patent: Nov. 9, 2004

(54) METHOD OF INHIBITING RETROVIRAL INTEGRASE

(75) Inventors: Christine C. Dykstra, Chapel Hill, NC (US); Ronald I. Swanstrom, Chapel Hill, NC (US); Richard R. Tidwell, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1826 days.

(21) Appl. No.: 08/185,079

(22) Filed: Jan. 20, 1994

(51) Int. Cl.$^7$ .............................................. A61F 31/415
(52) U.S. Cl. ...................... 514/394; 514/394
(58) Field of Search ........................................ 514/394

(56) References Cited

U.S. PATENT DOCUMENTS

| | | | |
|---|---|---|---|
| 4,933,347 A | 6/1990 | Tidwell et al. | 514/256 |
| 4,963,589 A | 10/1990 | Tidwell et al. | 514/636 |

FOREIGN PATENT DOCUMENTS

| | | |
|---|---|---|
| WO | WO95/08540 | 3/1995 |

OTHER PUBLICATIONS

S.L. Vonderfecht et al; *Protease Inhibitors Suppress the in Vitro and in Vivo Replication of Rotavirus*; J. Clin. Invest. 82: 2011–2016 (1988).

T.A. Fairley et al; *Structure, DNA Minor Groove Binding, and Base Pair Specificity of Alkyl–and Aryl–Linked Bis (amidinobenzimidazoles) and Bis(amidinoindoles)*; J. Med. Chem. 36; 1746–1753 (1993).

Robert L. LaFemina et al.; *Requirement of Active Human Immunodeficiency Virus Type 1 Integrase Enzyme for Productive Infection of Human T–Lymphoid Cells*; Journal of Virology 66; Dec. 1992; pp. 7414–7419.

Mark R. Fesen et al.; *Inhibitors of Human Immunodeficiency Virus Integrase*; Proc. Natl. Acad. Sci. USA 90; Mar. 1993; pp. 2399–2403.

*Primary Examiner*—Russell Travers
*Assistant Examiner*—Mary Peoples
(74) *Attorney, Agent, or Firm*—Jenkins, Wilson & Taylor, P.A.

(57) ABSTRACT

Disclosed is a method of inhibiting retroviral integrase in a subject in need of such treatment. The method comprises administering to the subject an effective retroviral integrase inhibiting amount of a bis-benzimidazole compound such as bis[5-amidino-2-benzimidazolyl]methane, 1,2-bis[5-amidino-2-benzimidazolyl]ethane, 1,2-bis[5-amidino-2-benzimidazolyl]ethene or a pharmaceutically acceptable salt thereof. A method for combatting retroviral infections is also disclosed.

20 Claims, 1 Drawing Sheet

METHOD OF INHIBITING RETROVIRAL INTEGRASE

FIELD OF THE INVENTION

The present invention relates to methods of inhibiting retroviral integrases with dicationic bis-benzimidazoles.

BACKGROUND OF THE INVENTION

The genome of the typical retrovirus encodes three primary enzymes that mediate the virus replication cycle. Reverse transcriptase converts the viral RNA genome into a double stranded DNA. Integrase nonspecifically inserts this DNA copy into the host cell genome, and protease cleaves viral structural and nonstructural proteins into their mature forms.

An essential step of the retroviral life cycle is the integration of its double-stranded DNA copy into the host genome. H. Sakai et al, *J. Virol.* 67, 1169–74 (1993). This process requires highly conserved sequence recognition and cleaving steps. For this reason, a therapeutic agent that can interrupt this process should be an effective and specific antiviral agent. A protein at the C-terminus of the viral polymerase, integrase (IN), is the only viral protein required for this process. R. LaFemina et al., *J. Virol.* 66, 7414–7419 (1992).

A. Fesen et al., *Proc. Natl. Acad. Sci. USA* 90, 2399–2403 (1993) discuss investigations using an in vitro integrase assay of a variety of chemicals as potential human immunodeficiency virus type I (HIV-1) integrase inhibitors. The article reports several topoisomerase inhibitors, such as doxorubicin, mitoxantrose, ellipticines and quercetin as potent inhibitors. While some topoisomerase inhibitors were excellent anti-integrase agents, no correlation was observed with antiviral effects. This is believed to be at least partially due to the fact that a number of topoisomerase inhibitors have severe cytotoxic effects, depending upon their mechansim of inhibition.

R. LaFemina et al., *J. Virology* 56, 7414–7419 (1992) reports studies assessing the usefulness of the integrase enzyme as a target for specific HIV-1 anti-viral therapeutic agents by determining its absolute requirement for productive HIV-1 infection. The article reports the results of the introduction of specific amino acid substitution into recombinant integrase and assesses the ability of the mutant proteins to properly mediate specific and non-specific cleavage as well as integration.

SUMMARY OF THE INVENTION

A first aspect of the present invention is a method of inhibiting retroviral integrase (e.g. in vitro, or in a subject in need of such treatment). The method comprises administering to the subject or contacting to the retroviral integrase an effective retroviral integrase-inhibiting amount of a compound according to Formula (I):

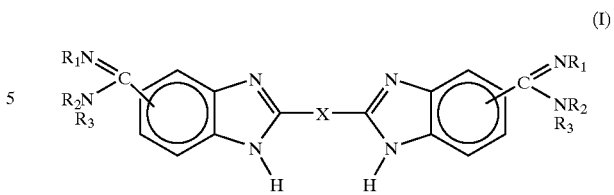

wherein:

$R_1$ and $R_2$ are each independently selected from the group consisting of H or lower alkyl, or $R_1$ and $R_2$ together represent —$(CH_2)_m$— wherein m is from two to four;

$R_3$ is H or lower alkyl; and

X is C1 to C2 saturated or unsaturated alkyl containing up to one double bond (e.g., —$(CH_2)_n$ wherein n is from 1–2, which is unsubstituted or substituted from 1 to 2 times with lower alkyl, and which is saturated or unsaturated and contains up to one double bond);

or a pharmaceutically acceptable salt thereof.

In a preferred embodiment of the invention, $R_1$ and $R_3$ are each H; $R_2$ is H or lower alkyl; and x is selected from the group consisting of —$CH_2$—$CH_2$— and —CH=CH— and any of the foregoing substituted from 1 to 2 times with lower alkyl; and the pharmaceutically acceptable salts thereof. Currently preferred compounds are bis[5-amidino-2-benzimidazolyl]methane; 1,2-bis[5-amidino-2-benzimidazolyl]ethane; 1,2-bis[5-amidino-2-benzimidazolyl]ethene; 1,2-bis[5-isopropylamidino-2-benzimidazolyl]ethene, or pharmaceutically acceptable salts thereof.

A second aspect of the present invention is a method of combatting a retroviral infection (e.g. in vitro, or in a subject in need of such treatment). The method comprises administering to the subject or contacting to the retrovirus an effective retroviral infection combatting amount of a compound according to Formula (I) as given above or a pharmaceutically acceptable salt thereof. Currently preferred compounds are bis[5-amidino-2-benzimidazolyl]methane; 1,2-bis[5-amidino-2-benzimidazolyl]ethane; 1,2-bis[5-amidino-2-benzimidazolyl]ethene; 1,2-bis[5-isopropylamidino-2-benzimidazolyl]ethene, or pharmaceutically acceptable salts thereof.

Compounds of formula I, or there pharmaceutically acceptable salts, may be included in a therapeutically effective amount in a pharmaceutically acceptable carrier to provide pharmaceutical formulations, with the therapeutically effective amount being effective to carry out the methods set forth above.

Further aspects of the present invention include the use of compounds of Formula (I) above and their pharmaceutically acceptable salts for the preparation of a medicament for inhibiting retroviral integrase, or for combatting a retroviral infection.

The foregoing and other objects and aspects of the present invention are explained in detail in the specification set forth hereinbelow.

DETAILED DESCRIPTION OF THE INVENTION

Figure 1:
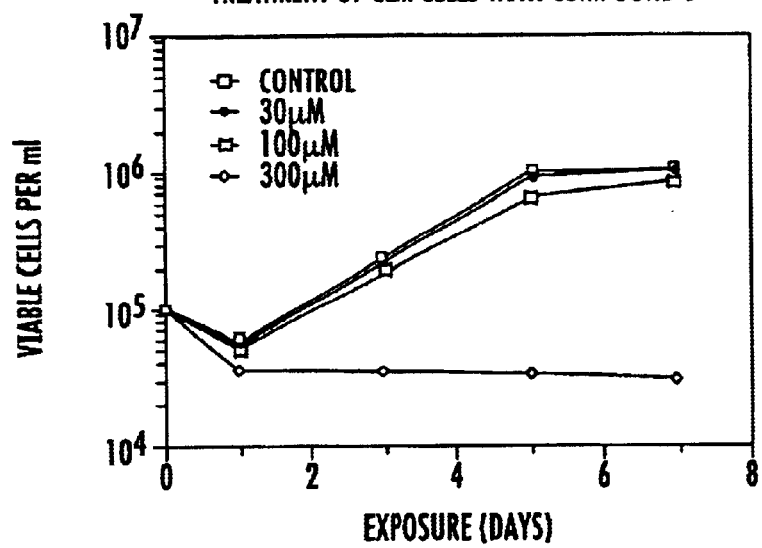
FIG. 1 shows the plating efficiency of CEM cells, a human T-lymphona cell line (A. H. Kaplan et al, *J. Virol.* 67, 4050–5 (1993)), treated with various concentrations of 1,2-bis[5-isopropylamidino-2-benzimidazolyl]ethene (Compound B) (30 $\mu$M, 100 $\mu$M, and 300 $\mu$M), the x-axis representing exposure time in days and the y-axis representing viable cells per milliliter (ml)

The term "lower alkyl," as used herein, refers to C1 to C4 linear or branched alkyl, such as methyl, ethyl, propyl, butyl, isopropyl, sec-butyl, and tert-butyl. Methyl and ethyl are preferred.

Subjects to be treated by the methods of the present invention are animal subjects, typically vertebrates, including both mammalian (e.g., human, cat, dog, cow, horse, sheep, pig, monkey, ape, etc.) and avian subjects (e.g., chicken, turkey, duck, goose, quail, pheasant, etc.).

The invention applies generally to retroviruses, i.e., the entire Retroviridae virus family. The family encompasses all viruses containing an RNA genome and an RNA-dependent DNA polymerase (reverse transcriptase) enzymatic activity. The family is divided into three subfamilies: (1) Oncovirinae, including all the oncogenic members and many closely related nononcogenic viruses; (2) Lentivirinae, the "slow" viruses, such as visna virus; and (3) Spumavirinae, the "foamy" viruses that induce persistent infections without any clinical disease. Retroviruses of interest include human retroviruses, such as immunodeficiency virus type 1 (HIV-1), avian retroviruses, such as avian sarcoma and leukosis viruses of chickens (ASLVs), endogenous viruses of certain pheasant and quail species, reticuloendotheliosis virus of turkeys and related viruses of ducks and chickens, and lymphoproliferate disease virus of turkeys; feline C-type retroviruses, including feline leukemia virus (FeLV) and feline sarcoma virus (FeSV) and endogenous retroviruses (RD114 and CCC isolates); mink C-type retroviruses, including mink leukemia virus (MiLV); porcine C-type retroviruses; horse C-type retroviruses, including the equine infectious anemia virus (EIAV); bovine C-type retrovirus, including enzootic bovine leukosis or lymphosarcoma; sheep C-type retroviruses; and primate retroviruses, including prosimian C-type retroviruses, Simian sarcoma and gibbon ape leukemia C-type retroviruses, baboon C-type retroviruses, macaque C-type retroviruses, owl monkey C-type retroviruses, Colobus monkey C-type retroviruses, Mason-Pfizer monkey D-type retrovirus, Langur D-type retrovirus and squirrel monkey D-type retrovirus. See N. Teich, Taxonomy of Retroviruses in *Molecular Biology of Tumor Viruses*, R. Weiss, N. Teich, H. Varmus, and J. Coffin, Eds., Cold Spring Harbor Laboratory, New York (2d ed. 1984), pps. 26–207.

As noted above, the present invention provides pharmaceutical formulations comprising the aforementioned compounds of Formula I, or pharmaceutically acceptable salts thereof, in pharmaceutically acceptable carriers, preferably for aerosol, oral, and parenteral administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of the present invention, will vary somewhat from compound to compound, patient to patient, and will depend upon the condition of the patient and the route of delivery. As a general proposition, a dosage from about 0.1 to about 20 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where salt is employed. Typically a dosage from about 0.56 mg/kg to about 5 mg/kg will be employed. In certain circumstances, higher or lower doses may be also appropriate. The duration of the treatment may be once per day for a period of from two to three weeks and may continue for period of months or even years, for example, in treating chronic conditions. Lower doses given less frequently can be used to prevent or reduce the incidence of recurrence of the infection. The daily dose can be administered either by a single dose in the form of an individual dosage unit or several smaller dosage units or by multiple administration of subdivided dosages at certain intervals.

Compounds of Formula (I) may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared form the following acids: hydrochloric, lactate, hydrobromic, sulfuric, nitric, phosphoric, maleic, acetic, salicylic, p-toluenesulfonic, tartaric, citric, methanesulfonic, formic, malonic, succinic, naphthalene-2-sulfonic and benzenesulfonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the retroviral integrase inhibiting agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

The formulations include those suitable for oral, rectal, topical, nasal, ophthalmic or parenteral (including subcutaneous, intramuscular and intravenous) administration. Formulations suitable for aerosol, oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the integrase inhibiting agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tables comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient and pyrogen-free.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

In accordance with the preferred embodiments of the present method, a compound of Formula I, or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

The present invention also provides pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts, an organic vehicle, such as glycerol, propylene, glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filing should be done by an aseptic method. Sterilized closures may then be placed on the vials and, if desired, the vial contents may be lyophilized.

In addition to compounds of Formula I or their salts, the pharmaceutical compositions may contain other additives, such pH adjusting additives. In particular, useful pH adjusting agents include acids or bases or buffers, such a sodium lactate, sodium acetate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provide an injectable, stable, sterile composition comprising a compound of Formula I, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into the subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous base emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well known in the art. When the compound of Formula I or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation.

These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds of salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose. Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds exemplary of Formula (I) above include, but are not limited to:

(A) 1,2-bis[5-amidino-2-benzimidazolyl]ethene;
(B) 1,2-bis[5-isopropylamidino-2-benzimidazolyl]ethene;
(C) bis[5-(2-imidazolyl)-2-benzimidazolyl]methane;
(D) bis[5-amidino-2-benzimidazolyl]methane;
(E) (5-Amidino-2-benzimidazolyl)-(5'-(2-imidazolinyl)-2'-benzimidazolyl)methane;
(AA) 1,2-bis[5-amidino-2-benzimidazolyl]ethane;
(BB) 1,2-bis[5-(2-imidazolyl)-2-benzimidazolyl]ethane;
(CC) 1,2-bis[5-(2-imidazolyl)-2-benzimidazolyl]ethene;
(DD) 1-(5-Amidino-2-benzimidazolyl)-(5'-(2-imidazolinyl)-2'-benzimidazolyl)ethane;
(EE) 1-(5-Amidino-2-benzimidazolyl)-(5'-(2-imidazolinyl)-2'-benzimidazolyl)ethene;
(FF) bis[5-isopropylamidino-2-benzimidazolyl]methane; and
(GG) 1,2-bis[5-isopropylamidino-2-benzimidazolyl]ethane.

Additional compounds illustrative of Formula (I) analogous to the foregoing can be produced by substituting a 2-pyrimidyl group for the 2-imidazolyl group.

Compounds employed in carrying out the present invention are either known or may be prepared in accordance with techniques known to those skilled in the art (see, e.g., U.S. Pat. No. 4,933,347, the entire disclosure of which is hereby incorporated by reference), particularly in light of the disclosure set forth below.

As indicated, the compounds used in the present invention may be present as pharmaceutically acceptable salts. Such salts include the glauconite, lactate, acetate, tartrate, citrate, phosphate, borate, nitrate, sulfate, and hydrochloride salts.

The salts of the present invention may be prepared, in general, by reacting two equivalents of the amidine base compound with the desired acid, in solution. After the reaction is complete, the salts are crystallized from solution by the addition of an appropriate amount of solvent in which the salt is insoluble.

The present invention will be further illustrated by the following non-limiting examples, in which "g" means grams, "mg" means milligrams, "$\mu$g" means micrograms, "mmol" means millimoles, "h" means hours, "ml" means milliliter, "M" means molar, "mM" means millimolar, "UV" means ultraviolet, "HCl" means hydrogen chloride, "NaCl" means sodium chloride, "EDTA" means ethylenediaminetetraacetic acid, "MP" means melting point, and "° C" means degrees Celcius.

EXAMPLE 1

Preparation of Compounds

The structures of the compounds used in the inhibition studies described below are given in Table 1 below. All were synthesized by previously published methods. See R. Tidwell et al, *Antimicrob. Agents and Chemother.* 38, 000–000 (1993); T. Fairley, *J. Med. Chem.* 36, 1746–1753 (1993).

TABLE 1

Structures of Integrase Inhibiting Compounds

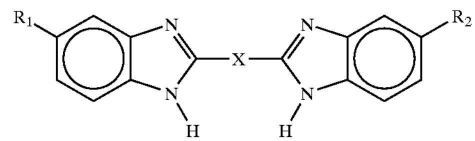

| Compound | $R_1$ | $R_2$ | X |
|---|---|---|---|
| A | Am | Am | —C═C— |
| B | IsopropAm | IsopropAm | —C═C— |
| C | Im | Im | $CH_2$ |
| D | Am | Am | $CH_2$ |
| E | Am | Im | $CH_2$ |

Am =

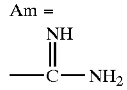

Im =

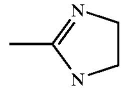

IsopropAm =

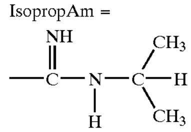

EXAMPLE 2

Preparation and Assay of Integrase Protein

Purification of Integrase Protein

Integrase was overproduced in *E. coli* from an inducible plasmid containing the integrase sequence under control of a lacI-regulated T7 polymerase using the integrase coding domain from the HXB2 clone of HIV-1 DNA (L. Ratner et al, *AIDS Res. Hum. Retroviruses* 3, 57–69 (1987)), pT7fll-IN. A one liter culture at an O.D. of 0.6 was induced by the addition of IPTG to 0.5 mM. After three hours, the cells were harvested by centrifugation and the pellets were stored at −70° C.

The integrase protein was purified by a modification of the method of Sherman and Fyfe (P. Sherman et al, *Proc. Natl. Acad. Sci. USA* 87, 5119–23 (1990)). The cells were lysed by thawing in a buffer (50 mM Tris-HCl pH 7.5, 5 mM dithiothreitol, 1 mM EDTA, 1 mg/ml lysozyme) on ice at 6 ml/g bacterial pellet for 30 minutes, and then incubating at 37° C. for 5 minutes. The lysate was centrifuged at 12,000×g for one hour. The pellets were resuspended in 50 mM Tris-HCl, pH 7.5, 1 mM dithiothreitol, 1 mM EDTA, 1 M NaCl (4 ml/g original bacteria). The homogenate was stirred for 30 minutes at 4° C. and recentrifuged for 30 minutes at 12,000×g.

The supernatant was made 0.8 M in ammonium sulfate by the slow addition of powder with stirring over a 30 minute period. The extract was then centrifuged to remove any precipitate and applied to a phenyl sepharose column. After a 50 ml wash with high salt buffer (50 mM Tris-HCl, 1 mM EDTA, 5 mM DTT, 2 M NaCl), the protein was eluted with a gradient from high salt to O salt buffer containing 10% (weight/vol) glycerol and further purified through a G75 Sephadex column to remove background nuclease. A one liter culture generates enough integrase activity to perform over a thousand drug inhibition assays.

Assays of Integrase Activity

The enzyme purification steps were monitored by an endonuclease/nicking assay and western blots utilizing a monoclonal antibody to integrase generated by W. Osheroff and R. Swanstrom at UNC—Chapel Hill. Supercoiled pBluescriptKS+II (0.3 $\mu$g) was incubated with column fractions in a buffer containing 20 mM Tris-HCl, pH 8.0, 5 mM 2-mercaptoethanol, and 2 mM $MnCl_2$ for 30 minutes at 37° C. The reactions were stopped by the addition of SDS to 1% and cleavage of the DNA substrate is assessed by electrophoresis through a 0.8% agarose gel stained with ethidium bromide and photographed under UV illumination.

Cleavage of specific sites is assessed as described in Sherman et al., supra, except that the assay buffer was the same as that reported by Chow et al, *Science* 255, 723–6 (1992). Single 20 mer oligonucleotides corresponding to either the U5 or U3 ends of HIV-1 are end-labeled with $^{32}P$, annealed with its complement, purified, and used under the same conditions as described above for the endonuclease assay. Reaction products are denatured with formamide, electrophoresed through 20% denaturing polyacrylamide gels and visualized by autoradiography. Both cleavage and ligation activity can be assessed from one gel. To assess the ligation activity alone, "precleaved" substrate that had the −2 cleavage artificially produced by using a radiolabelled 18 mer oligonucleotide was also used for some experiments.

EXAMPLE 3

Virus and Cell Cultures

Cell lines used were CEM cells, a human T-cell lymphona cell line, A. Kaplan et al, *J. Virol.* 67, 4050–5 (1993), and Magic cells, J. Kimpton et al, *J. Virol.* 66, 2232–2239 (1992). The CEM cells were grown in RPM1-1640 medium supplemented with 5% FCS. The Magic Cells, a HELA derivative, were grown in DMEM/H supplemented with 5% FCS, G418 (20 mg/ml) and Hygromycin (10 mg/ml). The HIV isolate was strain HXB2, originally from Lee Ratner in the laboratory of Robert Gallo at the National Institutes of Health.

EXAMPLE 4

Toxicity Assays

Three different toxicity tests were performed on the cell lines used to measure virus infectivity.

The initial test for toxicity utilized the XTT Assay as described by Weislow et al, *J. Natl. Cancer Inst.* 81, 577–586 (1989). This is the standard assay used originally to measure cell toxicity by potential reverse transcriptase inhibitors. Briefly, cells were grown to cells/ml and drug dilutions were added to the medium. After two days incubation, XTT reagent is added and incubation is continued for 4 h at 37° C. Following incubation, the plates are read at 450 minus 650 nm (the 650 value is the backround value which is automatically subtracted) with controls of media+XTT reagent without cells, and cells+media without reagent. Also a control of cells+media+XTT reagent was run for each plate. Medium without phenol red was employed to minimize background color as the XTT reagent goes from colorless (unreduced) to orange (reduced). The XTT reagent was freshly prepared on the day of assay as follows: 1 mg/ml of XTT in 0.01 M phenazine methosulfate. The phenazine methosulfate solution was prepared ahead of time and stored at 4° C. in a dark bottle. The XTT reagent is added to the microtiter wells at 24 ul per 100 ul of medium. The O.D. was measured on a Vmax plate reader from Molecular Devices Co. with data reduction. Results are expressed as percent of untreated controls. The least toxic compounds were Compounds A, B, and F with toxicities values at 500 $\mu$M or greater.

Next, a plating efficiency test measured the ability of the cell to grow after incubation with drug for a number of days. Magic cells were grown from an initial cell concentration of 0.8×104 with or without various concentrations of test compound for 6 days. Plating ability of the cells was assessed by plating dilutions of each culture on plastic. Colony forming units were determined after growth for two to four days by counting colonies after staining the plates. Each sample was plated in duplicate and the colony number averaged. The results are set forth in FIG. 1.

Figure 2:
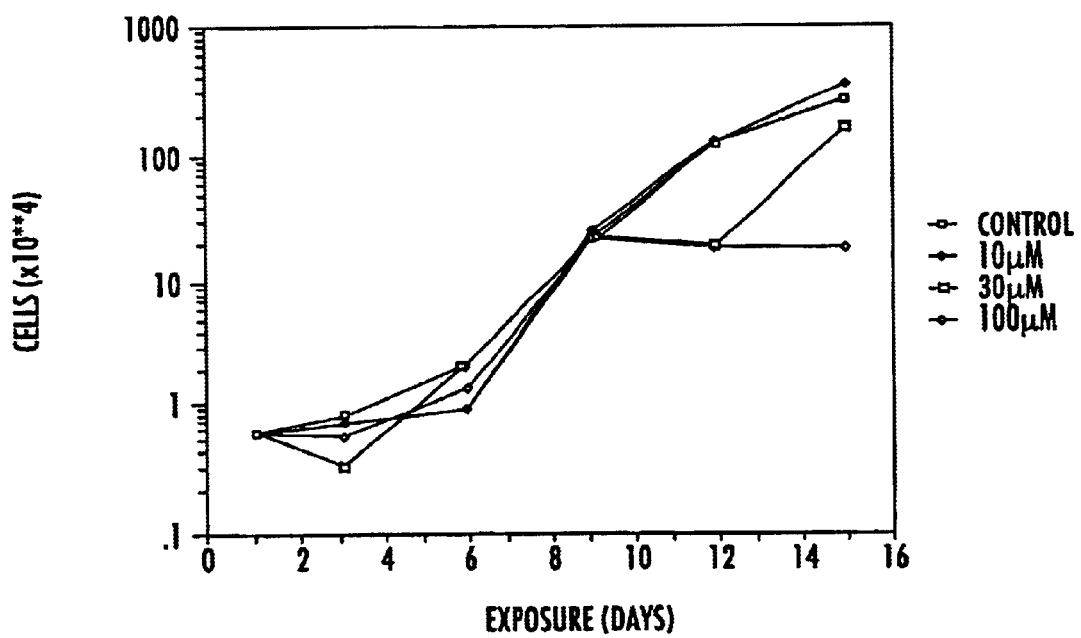
FIG. 2 shows the growth rate of Magic cells (J. Kimpton et al, *J. Virol.* 66, 2232–2239 (1992)) in the presence of various concentrations of 1,2-bis[5-isopropylamidino-2-benzimidazolyl]ethene (Compound B) (10 $\mu$M, 30 $\mu$M, and 100 $\mu$M), the x-axis representing exposure time in days and the y-axis representing the number of cells.

The third test for cell toxicity assessed growth rate in the presence of the test compound versus a control culture. Magic cells were grown over a period of 15 days with or without various dilutions of test compound. Aliquots were removed every other day and the cells were counted in a hemocytometer. The results are set forth in FIG. 2 herein (see also Table 2 below).

EXAMPLE 5

Integrase Inhibition Assays

Testing As Integrase Inhibitors

Integrase overproduced in *E. coli* was purified as described above in accordance with Sherman et al, supra, and used in drug inhibition assays. The integrase preparation used for these studies was extremely pure and did not contain any contaminating nuclease activity. Dilutions of the inhibitor compounds described in Example 1 above were mixed with substrate before the addition of enzyme. The Assay was the same as described in Example 2 and used the substrate described in Example 2. Each assay was performed in duplicate. Radioactivity in bands on dried gels were quantitated with a Phosphor imager to assess drug effects on both the cleavage, nuclease, and ligation products. The $IC_{50}$ values for integrase inhibition were calculated for both the cleaving and joining parts of the integrase reaction after determining the % inhibition of the control reaction for a series of drug concentrations. These results are shown in Table 2 below. Compounds A, B, C, and D had similar effects on integrase activity. Compound A, however, caused aggregation of the substrate starting at relatively low concentrations (10 μM), complicating its assessment.

TABLE 2

Summary of $IC_{50}$s (μM)

| Drug | Magic Cells | | Integrase[1] | |
| --- | --- | --- | --- | --- |
| | HIV-1 | Toxicity | Cleavage | Strand Transfer |
| A[2] | 48 | >500 | 11 | 11.5 |
| B | 10–30 | 473.2 | 61 | 19 |
| C | 16 | 237.9 | 64 | 22 |
| D | 7 | 175.3 | — | — |
| E | 16 | 65 | >100 | 122 |

[1]Activity was measured at the % cleavage of the substrate compared to control.
[2]This drug caused aggregation of the substrate and also precipitated out of the culture medium at higher drug concentrations.

Although not wishing to be bound by any theory or explanation of the invention, these compounds are currently believed to bind in the double stranded DNA minor groove with an AT bias (see T. Fairley et al, *J. Med. Chem.* 36, 1746–1753 (1993)), and most likely inhibit integrase by preventing the binding of integrase to its recognition sequences at the long terminal repeat ("LTR") of the virus. This proposed mechanism is supported by the observation that both cleavage and integration are equally effected by the compounds. Either DNA sequence specificity and/or direct interactions with the integrase protein are also currently believed to be possibly involved in the compound mechanism. Since integrase functions as a multimer, K. S. Jones et al, *J. Biol. Chem.* 267, 16037–40 (1992), it is also possible that the DNA binding of the compounds somehow effects the multimer equilibrium.

The results indicate that DNA binding strength alone, however, is not the determining factor. Either DNA sequence specificity and/or direct interactions with the integrase protein are currently also believed to be possibly involved. Since nucleosomes have been shown to be precisely positioned in the 5' LTR of HIV-1, A. Fesen et al., *Proc. Natl. Acad. Sci. USA* 90, 2399–2403 (1993), such phasing could be one other way that the dicationic, groove binding drugs interfere with integrase action.

EXAMPLE 6

HIV-1 Inhibition Assays

The magic cell assay described by Kimpton et al., supra, was used as described. This assay identifies individual cells infected with HIV-1 by the expression of tat, which transactivates an endogenous copy of the HIV-1 LTR linked to the lac2 reporter gene after integration, inducing β-galactosidase expression when x-gal is added to the cell medium. Any cell with integrated HIV-1 will turn blue. Thus, this assay provides a convenient way to determine the effect of HIV inhibitors at any early step up through the expression of tat, including the inhibition of integration.

The magic cells are plated in twelve-well plates one day prior to infection. The standard assay involves infection with approximately 200 infectious units of HIV-1. This gives an approximately 20 to 1 ratio of signal to background and sufficient numbers of infectious events to quantitate dim effects. The cells are pretreated with drug for 4 hours prior to virus infection, and virus adsorption takes place for 1 hour. The cells are washed with plain medium, and then medium with inhibitor is placed back on the cells. Two days later the cells are fixed after integration with x-gal, the indicator reagent for β-galactosidase production. The number of β-galactosidase expressing cells are quantitated by light microscopy.

The results of comparisons of infectious units with or without various concentrations of the bis-benzimididazoles drugs in the magic cell assay are expressed as $IC_{50}$ values and are compiled in Table 2 above. Note that the best anti-HIV compounds (B–D) were also the best integrase inhibitors, except for compound A, which could not be accurately measured due to its substrate aggregating properties.

In addition, the assessment of antiviral activity as measured by the standard reinfection assay was performed for compound B. The $IC_{50}$ for compound B in this assay was 10–30 μM. This confirms that the Magic cell assay is suitable for screening potential integrase inhibitors with good antiviral activity.

Another test of cellular effects by the compounds was a measure of plating efficiency of the cells after incubation with various concentrations of test agents. This will assess the actual killing of the cells by the drugs. The $IC_{50}$ values are expected to be much higher in this test. The results indicate that the best anti-HIV compound, B, had no effect on the Magic cell plating efficiency at the concentrations at which anti-viral effects were observed.

The most sensitive test employed measurements of growth rates for the cells in the presence of the test compound. Although the anti-viral assay used was one that assessed early times of the viral life cycle, this test was carried out for 15 days, with counting of cell numbers in cultures performed every other day during this time. It is important to note that for up to two weeks, the concentration of Compound B that inhibited 50% of the viral integration events had no effect on the growth rate of the cell line. Higher concentrations, however, did effect the growth rate of the cells.

The foregoing examples are illustrative of the present invention, and are not to be construed as limiting thereof. The invention is defined by the following claims, with equivalents of the claims to be included therein.

That which is claimed is:

1. A method of combating a retroviral infection in a subject having a retroviral infection, comprising administering to said subject an effective retroviral infection combatting amount of a compound according to Formula (I):

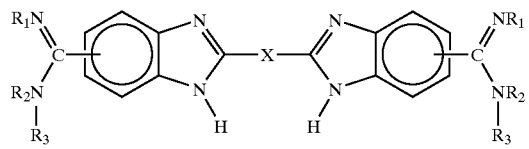

wherein:
R$_1$ and R$_2$ are each independently selected from the group consisting of H or lower alkyl, or R$_1$ and R$_2$ together represent —(CH$_2$)$_m$— wherein m is from two to four;
R$_3$ is H or lower alkyl; and
X is C1 to C2 saturated or unsaturated alkyl containing up to one double bond;
or a pharmaceutically acceptable salt thereof.

2. A method according to claim 1, wherein $R_1$, $R_2$, and $R_3$ are H.

3. A method according to claim 1, wherein $R_1$ and $R_2$ together represent —$CH_2$—$CH_2$— and $R_3$ is H.

4. A method according to claim 1, wherein X is —$(CH_2)_n$— wherein n is from 1 to 2, which is unsubstituted or substituted from 1 to 2 times with lower alkyl, and which is saturated or unsaturated and contains up to one double bond.

5. A method according to claim 1, wherein X is selected from the group consisting of —$CH_2$—$CH_2$—, —CH=CH—, and any of the foregoing substituted from 1 to 2 times with lower alkyl.

6. A method according to claim 1, wherein said compound is selected from the group consisting of:

(A) 1,2-bis[5-amidino-2-benzimidazolyl]ethene;
(B) 1,2-bis[5-isopropylamidino-2-benzimidazolyl]ethene;
(C) bis[5-(2-imidazolyl)-2-benzimidazolyl]methane;
(D) bis[5-amidino-2-benzimidazolyl]methane;
and the pharmaceutically acceptable salts thereof.

7. A method according to claim 1, wherein said compound of Formula I is bis[5-amidino-2-benzimidazolyl]methane or a pharmaceutically acceptable salt thereof.

8. A method according to claim 1, wherein said compound of Formula I is 1,2-bis[5-amidino-2-benzimidazolyl]ethane or a pharmaceutically acceptable salt thereof.

9. A method according to claim 1, wherein said compound of Formula I is 1,2-bis[5-amidino-2-benzimidazolyl]ethene or a pharmaceutically acceptable salt thereof.

10. A method according to claim 1, wherein the subject is mammalian.

11. A method according to claim 1, wherein the subject is avian.

12. A method of treating HIV infection in a subject having an HIV infection, comprising administering to said subject an effective HIV infection combatting amount of a compound according to Formula (I):

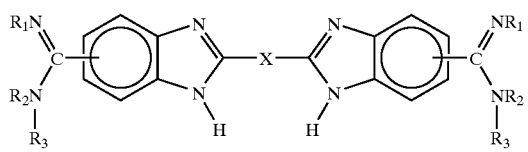

wherein:

$R_1$ and $R_2$ are each independently selected from the group consisting of H or lower alkyl, or $R_1$ and $R_2$ together represent —$(CH_2)_m$— wherein m is from two to four;

$R_3$ is H or lower alkyl; and

X is C1 to C2 saturated or unsaturated alkyl containing up to one double bond;

or a pharmaceutically acceptable salt thereof.

13. A method according to claim 12, wherein $R_1$, $R_2$, and $R_3$ are H.

14. A method according to claim 12, wherein $R_1$ and $R_2$ together represent —$CH_2$—$CH_2$— and $R_3$ is H.

15. A method according to claim 12, wherein X is —$(CH_2)_n$— wherein n is from 1 to 2, which is unsubstituted or substituted from 1 to 2 times with lower alkyl, and which is saturated or unsaturated and contains up to one double bond.

16. A method according to claim 12, wherein X is selected from the group consisting of —$CH_2$—$CH_2$—, —CH=CH—, and any of the foregoing substituted from 1 to 2 times with lower alkyl.

17. A method according to claim 12, wherein said compound is selected from the group consisting of:

(A) 1,2-bis[5-amidino-2-benzimidazolyl]ethene;
(B) 1,2-bis[5-isopropylamidino-2-benzimidazolyl]ethene;
(C) bis[5-(2-imidazolyl)-2-benzimidazolyl]methane;
(D) bis[5-amidino-2-benzimidazolyl]methane;
and the pharmaceutically acceptable salts thereof.

18. A method according to claim 12, wherein said compound of Formula I is bis[5-amidino-2-benzimidazolyl]methane or a pharmaceutically acceptable salt thereof.

19. A method according to claim 12, wherein said compound of Formula I is 1,2-bis[5-amidino-2-benzimidazolyl]ethane or a pharmaceutically acceptable salt thereof.

20. A method according to claim 12, wherein said compound of Formula I is 1,2-bis[5-amidino-2-benzimidazolyl]ethene or a pharmaceutically acceptable salt thereof.

* * * * *